United States Patent [19]

Wang

[11] Patent Number: 4,459,411

[45] Date of Patent: Jul. 10, 1984

[54] PREPARATION OF UNSATURATED HETEROCYCLIC CARBONYL-CONTAINING COMPOUNDS

[75] Inventor: Pen C. Wang, Midland, Mich.

[73] Assignee: The Dow Chemical Company, Midland, Mich.

[21] Appl. No.: 417,274

[22] Filed: Sep. 13, 1982

[51] Int. Cl.$^3$ .................... C07D 233/20; C07C 1/00
[52] U.S. Cl. ................. 548/229; 204/59 R; 548/317; 548/320; 548/543
[58] Field of Search ............ 548/229, 230, 317, 543; 204/59 R, 72, 78

[56] References Cited

U.S. PATENT DOCUMENTS

| | | | |
|---|---|---|---|
| 3,887,577 | 6/1975 | Dixon | 548/315 |
| 4,087,611 | 5/1978 | Raghu et al. | 548/229 |
| 4,140,593 | 2/1979 | Mitzlaff | 204/59 R |
| 4,322,271 | 3/1982 | Jensen et al. | 204/73 R |

FOREIGN PATENT DOCUMENTS 9697  4/1980  European Pat. Off. .

OTHER PUBLICATIONS

T. Shono et al., J.A.C.S., 97, 4264 (1975).
James, T. K.: Woo et al., J. Polymer Sci., B, 7, 181 (1969).
Hartmann et al., Liebigs Ann. Chem., 1319 (1976).
Duschinsky et al., J.A.C.S., 2350 (1946).
Scholz et al., Ann. Chem. 1976, pp. 1319–1322.

*Primary Examiner*—John F. Niebling
*Attorney, Agent, or Firm*—Douglas N. Deline

[57] ABSTRACT

Unsaturated heterocyclic carbonyl-containing compounds, e.g., 2H-imidazol-2-ones, 2(3H)-oxazolones and 2H,3H-pyrrol-2-ones, are prepared by the anodic oxidation of saturated heterocyclic carbonyl-containing precursors of the above compounds in a $C_{1-4}$ alcohol or carboxylic acid solvent in the presence of a supporting electrolyte followed by dehydrosubstitution of the alkoxy- or acyloxy-substituted intermediate.

The products formed may be polymerized or copolymerized with other ethylenically unsaturated monomers to prepared resins, films, etc. or they may be employed as intermediates for the preparation of various biologically active compounds.

13 Claims, No Drawings

PREPARATION OF UNSATURATED HETEROCYCLIC CARBONYL-CONTAINING COMPOUNDS

BACKGROUND OF THE INVENTION

The present invention relates to a process for preparing unsaturated heterocyclic compounds containing carbonyl functionality. More particularly, the present process employs an electrochemical oxidation of saturated heterocyclic precursors in solution followed by elimination of the oxidatively added substituent along with adjacent hydrogen to prepare the desired unsaturated functionality.

T. Shono et al., *J.A.C.S.*, 97, 4264 (1975) prepared linear α-methoxy-substituted urethanes by anodic oxidation of methyl N-alkyl-substituted carbamates in methanol. The compounds were found to demethanolate under acidic or thermolytic conditions, Id., at 4266, column 2, 6th paragraph.

In European Patent No. 9,697, the anodic oxidation of certain carbamates including 2-oxazolidinone in methanol solution to prepare α-methoxy-substituted urethane derivatives was disclosed, Id., at page 4, line 27. The reference further taught at page 13, line 13 that the α-methoxy-substituted urethanes prepared may be used as starting material to prepare vinyl urethanes suitable for preparing polymers as disclosed by James T. K. Woo et al., *J. Polymer Sci., B*, 7, 181 (1969). The latter reference taught the use of a variety of N-vinyl compounds including N-vinyl pyrrolidone in radiation-induced polymerizations.

In U.S. Pat. No. 4,322,271, N-vinyl-N-alkyl carboxylic acid amides were prepared by the anodic oxidation of N-ethyl carboxylic acid amides followed by a splitting off of alcohol functionality. The reference provides a thorough discussion of known techniques of splitting off alcohol functionality for which teaching the above patent is incorporated in its entirety by reference.

Previous methods of preparing unsaturated heterocyclic carbonyl compounds have not proven acceptable for commercial implementation. Hartmann and co-workers, *Liebigs Ann. Chem.*, 1319 (1976), prepared 3-acetyl-2(3H)-oxazolones by the photochlorination of 3-acetyl-2-oxazolidinones in carbon tetrachloride solution, followed by dehydrochlorination of the resulting product. A yield of 50 percent was obtained.

Imidazol-2-ones have been prepared by several techniques. The most common preparation involves the cyclization of an aminoketone or aldehyde derivative with KOCN or HOCN. See, e.g., Duschinsky et al., *J.A.C.S.*, 2350 (1946), or Ger. Offen. No. 2,718,058.

Unsaturated heterocyclic compounds containing carbonyl functionality are useful monomers for polymerization and copolymerization processes, e.g., to prepare polyethyleneamines or poly(1-amino-2-hydroxyethylene) resins and films that have uses in metal chelation, gas conditioning and other applications. Particular compounds are also capable of use in special applications. For example, imidazol-2-ones are known to possess useful bacteriostatic activity and may be converted to 2-imino derivatives of substituted imidazolones that are known plant growth regulators as taught by U.S. Pat. No. 3,887,577. The compounds are further useful as intermediates in the preparation of pharmaceuticals and other fine organics.

Prior methods of anodic oxidation have been concerned with the preparation of α-alkoxy-substituted compounds and N-vinyl-substituted derivatives thereof. To the best of my present knowledge no attempt has been made to prepare unsaturated heterocyclic carbonyl-containing compounds by an electrochemical oxidation followed by elimination of alcohol or acid groups to prepare cyclic unsaturation.

It would be desirable to provide a process for the preparation of 2H-pyrrol-2-one, 2(3H)-oxazolone and 2H-imidazol-2-one compounds from the corresponding saturated precursors: 2-pyrrolidinone, 2-oxazolidinone and imidazolidine-2-one compounds.

It would further be desirable to provide such a process that avoids the formation of inorganic or organic salt by-products but rather results in the formation of useful by-products under neutral reaction conditions.

Finally, it would be desirable to provide a process that allows the facile recovery of the desired product in high yields and purity.

SUMMARY OF THE INVENTION

According to the present invention there is provided a process for preparing unsaturated cyclic carbonyl-containing compounds corresponding to the formula:

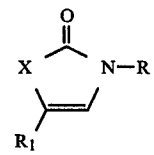

wherein
 X is $>CH_2$, $-O-$, or $>N-R$;
 R is hydrogen, lower alkyl or acyl; and
 $R_1$ is hydrogen or lower alkyl,
comprising the steps of
 (a) anodically alkoxylating or acyloxylating a cyclic precursor corresponding to the formula:

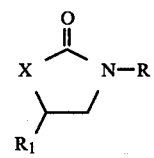

wherein X, R and $R_1$ are as defined above, with an alcohol or carboxylic acid of the formula R'OH wherein R' is $C_{1-4}$ alkyl or acyl, in an electrolysis cell in the presence of a supporting electrolyte to produce an alkoxy- or acyloxy-substituted intermediate corresponding to the formula:

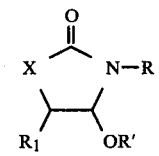

wherein X, R, $R_1$ and R' are as above-defined; and
 (b) dehydrosubstituating the substituted intermediate by splitting off from the alkoxy- or acyloxy-substituted intermediate an alkanol or carboxylic acid corresponding to the formula R'OH, wherein R' is as above-defined.

DETAILED DESCRIPTION OF THE INVENTION

Anodic oxidation processes are now well-known and detailed description of the conditions of operation need not be provided. The teachings of German Offen. No. 2,113,338, the previously cited U.S. Pat. No. 4,322,271 and European Patent No. 9,697 are hereby incorporated by reference as teaching the well-known details of the process.

In general, the cyclic precursor that is to be oxidized is placed in an electrolysis cell containing the $C_{1-4}$ alkanol or $C_{1-4}$ carboxylic acid and a supporting electrolyte. Preferred $C_{1-4}$ alkanols or carboxylic acids are methanol, ethanol or acetic acid. Most preferred is methanol. Cyclic precursors are well-known and commercially available or they may be prepared by known techniques.

Preferred cyclic precursors are ethylene urea and 5-alkyl-substituted ethylene ureas suitable for the preparation of 2H-imidazol-2-ones and 5-methyl-2H-imidazol-2-ones; and 2-oxazolidinone and 3-alkyl-2-oxazolidinones suitable for the preparation of 2(3H)-oxazolones and 3-alkyl-2(3H)-oxazolones.

The supporting electrolyte is a conducting salt selected to provide the necessary conductivity and to be otherwise inert towards the formation of by-products. To be effective, the electrolyte should readily disassociate in the electrolysis cell. Suitable supporting electrolytes are well-known in the art and generally include alkali metal, alkaline earth metal, ammonium and quaternary ammonium salts of perchloric acids, tetrafluoroborohydrate, hexafluorophosphoric acid, hydrofluoric acid, nitric acid, lower carboxylic acids, lower alkyl sulfonic acids or $C_{6-12}$ aryl sulfonic acids. Acetic acid salts are particularly effective in acetic acid solvent whereas quaternary ammonium salts of p-toluene sulfonic acid are otherwise preferred. Mixtures of conducting salts may also be employed.

The conducting salt is generally present in minor amounts of at least about 0.1 percent by weight based on the total electrolysis solution. Preferred is an amount from about 1 percent to about 20 percent by weight.

The $C_{1-4}$ alkanol or carboxylic acid is employed both as reactant and solvent. Generally molar ratios of cyclic precursor to $C_{1-4}$ alcohol or carboxylic acid from about 1:1 to about 1:100 are employed. Preferred is a ratio from about 1:2 to about 1:50.

While the above three components have been described as present during the anodic oxidation process, additional compounds are not necessarily prohibited. Small amounts of water may be present without deleteriously affecting the course of the reaction. It may also be beneficial when employing an alkanol to provide a small amount of basic material, particularly a base that is resistant to oxidation such as 2,6-lutidine, to help in stabilizing the reactant and products against a drop in pH. Of course, the components of the process need not be combined in any particular order.

The anodic oxidation is effected by passing an electric current through the electrolytic solution by means of electrodes. The cathode is generally constructed of base metals such as steel, nickel, copper and the like, or carbon. Anodes are generally formed of inert conducting materials such as carbon (such as in the form of graphite, vitreous carbon, etc.), lead dioxide or noble metals and alloys thereof, or base metals coated with a noble metal. A preferred cathodic material is steel. A preferred anodic material is carbon.

The anodic oxidation is carried out at temperatures from about $-20°$ C. to about the boiling point of the electrolytic solution. Preferred temperatures are from about 0° C. to about 60° C. Current densities of from about 0.01 to about 1 A/cm$^2$, and cell voltages from about 4 to about 15 volts are suitably employed. Additional features such as the shape of the electrodes, the presence of cell divisions such as by diaphragms to form separate anodic and cathodic chambers, and use of continuous processes may be selected according to the convenience of the operator.

Ordinarily atmospheric pressure is employed, however, elevated or reduced pressure may also be selected although no advantage is known to result therefrom. It may, however, be advantageous from a safety standpoint to provide a means of purging the cell with an inert sweep gas inasmuch as the product formed at the cathode during the process is hydrogen gas which should be removed from the system to avoid an explosion hazard.

A substantially complete conversion of starting material simplifies efforts to recover the alkoxy- or acyloxy-substituted intermediate. In that regard, the quantity of current supplied to the cell should be about 2 Faradays per mole of alkoxy or acyloxy groups reacted. Over-oxidation to yield undesired by-products may occur at higher current values.

When the anodic alkoxylation or acyloxylation is substantially complete, the electrolysis is terminated, preferably by a step-wise diminution of current. Remaining alkanol or carboxylic acid, if any, is removed by distillation leaving relatively pure alkoxy- or acyloxy-substituted intermediate and precipitated supporting electrolyte.

The dehydrosubstituating process or splitting process can often be carried out according to known techniques. Many of the alkoxy- or acyloxy-substituted intermediates may be dehydrosubstituated by simple pyrolysis optionally in the presence of a catalyst. The intermediate is heated to a temperature from about 60° C. to about 375° C. and preferably from about 150° C. to about 350° C. Catalytic substances for the splitting process include weakly acidic metal oxides such as the oxides of Al, Be, Zr and W. Also the weakly acid phosphates of Ca, Al, Mo, B and W; aluminosilicates in the H form including zeolites; and ammonium salts such as halides, sulfates and phosphates. Conditions and reaction procedures for such pyrolytic dehydrosubstituation are known in the art and need not be further described.

Occasionally, in order to protect the alkoxy- or acyloxy-substituted intermediate from decomposition under the conditions of the pyrolysis, it may be necessary to protect the nitrogen by substitution with a protecting group if not already alkyl-substituted. Suitable easily removable protecting groups include acetyl or silyl groups that may be added even prior to the anodic oxidation step if desired.

The pyrolysis may be accomplished in a single step as part of the distillation of electrolysis products remaining in the cell after termination of the anodic oxidation process, thereby eliminating the need to recover the alkoxy- or acyloxy-substituted intermediate as a separate process step.

As an alternative to pyrolysis it is also possible to dehydrosubstituate the alkoxy- or acyloxy-substituted intermediates by reaction with acetic anhydride, optionally with a catalyst such as an alkali metal acetate. In the event the nitrogen groups are not substituted, treatment in this manner will acylate the nitrogen and at the same time split off the alkanol or carboxylic acid necessary to form the desired unsaturation.

SPECIFIC EMBODIMENTS

Having described the invention, the following examples are provided as further illustrative of the invented process and are not to be construed as limiting.

EXAMPLE 1

Preparation of 1,3-diacetyl-2H-imidazol-2-one

Ac—N—C(=O)—N—Ac (imidazol-2-one ring)

Into an 80-ml undivided electrolysis cell (beaker) fitted with two platinum (2 cm×2 cm) electrodes is placed 4.3 g (0.05 mole) of ethylene urea, 0.32 g (0.0015 mole) of tetraethylammonium fluoroborate as a supporting electrolyte and 50 ml of methanol as solvent. The constant current (0.5A) at a terminal voltage of about 20-30 v. through the cell which is externally cooled with water. After two Faradays/mole of electricity are passed, methanol is removed under reduced pressure. The residue is treated with excess acetic anhydride and a catalytic amount of sodium acetate and heated at 110° C.–120° C. The progress of the reaction may be monitored by gas/liquid chromatography and the desired 1,3-diacetyl-2H-imidazol-2-one isolated by distillation or sublimation as long needles after removal of acetic anhydride. Product identity is confirmed by nuclear magnetic resonance spectroscopy. Overall yield is 40 percent. Acetate functionality may be easily removed by treatment with strong bases such as an alkali metal alkoxide, etc.

EXAMPLE 2

Preparation of 1,3-diacetyl-5-methyl-2H-imidazol-2-one

Ac—N—C(=O)—N—Ac, with H₃C substituent on ring

The reaction conditions of Example 1 are substantially repeated excepting that 5-methylethylene urea is substituted in place of ethylene urea. Overall yield of 1,3-diacetyl-5-methyl-2H-imidazol-2-one is 50 percent.

EXAMPLE 3

Preparation of 3-acetyl-2(3H)-oxazolone

O—C(=O)—N—Ac (oxazolone ring)

The reaction conditions of Example 1 are substantially repeated excepting that 2-oxazolidinone is substituted in place of ethylene urea. Overall yield of 3-acetyl-2(3H)-oxazolone is 50 percent.

Example 4

Preparation of 3-acetyl-5-ethyl-2(3H)-oxazolone

O—C(=O)—N—Ac (oxazolone ring, ethyl substituent)

The reaction conditions of Example 1 are substantially repeated excepting that 5-ethyl-2-oxazolidinone is substituted in place of ethylene urea. Overall yield of 3-acetyl-5-ethyl-2(3H)-oxazolone is 30 percent.

EXAMPLE 5

Preparation of 3-ethyl-2(3H)-oxazolone

O—C(=O)—N—C₂H₅ (oxazolone ring)

Into 250 ml of undivided electrolysis cell (beaker) fitted with two carbon electrodes is placed 10.07 g (0.0876 mole) of N-ethyl-2-oxazolidinone, 1.0 g (0.0032 mole) of tetraethylammonium-p-toluene sulfonate as a supporting electrolyte and 50 ml of methanol as a solvent. The constant current (0.5A) is passed through the cell which is externally cooled with H₂O. After 2 Faradays/mole electricity are passed, methanol is removed under reduced pressure. The residue is fractionated for isolation of 3-ethyl-2(3H)-oxazolone (130° C., 10 mm). The progress of the electrolysis reaction can be monitored by gas/liquid chromatography and the structure of 3-ethyl-2(3H)-oxazolone is confirmed by nuclear magnetic resonance spectral data. Overall yield from N-ethyl-2-oxazolidinone is 75 percent.

EXAMPLE 6

Preparation of 3-methyl-2(3H)-oxazolone

O—C(=O)—N—CH₃ (oxazolone ring)

The reaction conditions of Example 3 are substantially repeated excepting that N-methyl-2-oxazolidinone is employed as the cyclic precursor. Overall yield of 3-methyl-2(3H)-oxazolone is 80 percent.

EXAMPLE 7

Preparation of 1-acetyl-2H,3H-pyrrol-2-one

CH₂—C(=O)—N—Ac (pyrrol-2-one ring)

If the reaction conditions of Example 1 are substantially repeated employing 2-pyrrolidinone as the cyclic precursor, the resulting product is 1-acetyl-2H,3H-pyrrol-2-one.

What is claimed is:

1. A process for preparing unsaturated cyclic carbonyl-containing compounds corresponding to the formula:

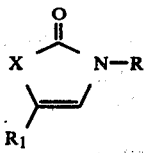

wherein
X is >CH$_2$, —O—, or >N—R;
R is hydrogen, lower alkyl or acyl; and
R$_1$ is hydrogen or lower alkyl,
comprising the steps of
(a) anodically alkoxylating or acyloxylating a cyclic precursor corresponding to the formula:

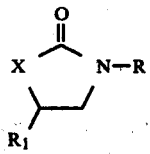

wherein X, R and R$_1$ are as defined above, with an alcohol or carboxylic acid of the formula R'OH wherein R' is C$_{1-4}$ alkyl or acyl, in an electrolysis cell in the presence of a supporting electrolyte to produce an alkoxy- or acyloxy-substituted intermediate corresponding to the formula:

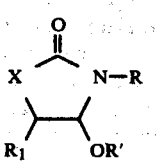

wherein X, R, R$_1$ and R' are as above-defined; and
(b) eliminating from the alkoxy- or acyloxy-substituted intermediate an alkanol or carboxylic acid corresponding to the formula R'OH, wherein R' is as above-defined.

2. A process according to claim 1 wherein the cyclic precursor is selected from the group consisting of ethylene urea, 5-alkyl-substituted ethylene urea, 2-oxazolidinone, 5-alkyl-substituted-2-oxazolidinone and 3-alkyl-substituted 2-oxazolidinones.

3. A process according to claim 1 wherein the cyclic precursor is anodically alkoxylated or acyloxylated in the presence of methanol, ethanol or acetic acid.

4. A process according to claim 3 wherein the cyclic precursor is alkoxylated.

5. A process according to claim 1 wherein the supporting electrolyte is selected from the group consisting of the alkali metal-, alkaline earth metal-, ammonium- and quaternary ammonium salts of perchloric acids; tetrafluoroborohydrate; hexafluorophosphoric acid; hydrofluoric acid; nitric acid; lower carboxylic acids; lower alkyl sulfonic acids and C$_{6-12}$ aryl sulfonic acids.

6. A process according to claim 4 wherein the supporting electrolyte is a quaternary ammonium salt of p-toluene sulfonic acid.

7. A process according to claim 1 wherein the supporting electrolyte is present in an amount from about 1 percent to about 20 percent by weight of the total electrolysis solution.

8. A process according to claim 1 wherein the molar ratio of cyclic precursor to C$_{1-4}$ alcohol or carboxylic acid is from about 1:2 to about 1:50.

9. A process according to claim 1 wherein the temperature is from about 0° C. to about 60° C.

10. A process according to claim 1 wherein the dehydrosubstituating process is accomplished by heating the alkoxy- or acyloxy-substituted intermediate to a temperature of from about 60° C. to about 375° C.

11. A process according to claim 10 wherein a splitting catalyst for the dehydrosubstituating process is additionally employed.

12. A process according to claim 1 wherein the dehydrosubstituating process is accomplished by contacting the alkoxy- or acyloxy-substituted intermediate with acetic anhydride.

13. A process according to claim 1 wherein X is —O— or >N—R.

* * * * *